(12) United States Patent
Sode et al.

(10) Patent No.: US 7,713,718 B1
(45) Date of Patent: May 11, 2010

(54) PROCESS FOR PRODUCING GLUCOSE DEHYDROGENASES

(75) Inventors: Koji Sode, Tokyo (JP); Hideaki Yamaoka, Kyoto (JP); Mitsuhiro Hoshijima, Kyoto (JP); Keisuke Kurosaka, Kyoto (JP); Shido Kawase, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 742 days.

(21) Appl. No.: 10/526,049

(22) PCT Filed: Aug. 20, 2003

(86) PCT No.: PCT/JP03/10541

§ 371 (c)(1),
(2), (4) Date: Sep. 28, 2005

(87) PCT Pub. No.: WO2004/020638

PCT Pub. Date: Mar. 11, 2004

(30) Foreign Application Priority Data

Aug. 30, 2002 (JP) ............................. 2002-253752

(51) Int. Cl.
*C12N 1/21* (2006.01)
*C07H 21/04* (2006.01)
(52) U.S. Cl. .................. 435/69.1; 435/252.3; 536/23.1
(58) Field of Classification Search ............... None
See application file for complete search history.

(56) References Cited

U.S. PATENT DOCUMENTS

2004/0023330 A1* 2/2004 Sode .......................... 435/69.1

FOREIGN PATENT DOCUMENTS

| EP | 1 498 484 | 1/2005 |
|---|---|---|
| JP | 2002-65778 | 3/2002 |
| JP | 2003-274964 | 9/2003 |
| WO | WO 02/36779 | 5/2002 |

OTHER PUBLICATIONS

Yamazaki et al. "Subunit Analyses of a Novel Thermostable Glucose Dehydogenase Showing Different Temperature Properties According to it Quaternary Structure". *Applied Biochemistry and Biotechnology*, vol. 77-79, pp. 325-335, 1999.

Inose et al., "Cloning and expression of the gene encoding catalytic subunit of thermostable glucose dehydrogenase from *Burkholderia cepacia* in *Escherichia coli*". *Biochimica et Biophysica Acta*, 1645 (2003), pp. 133-138.

Stover et al., "Complete genome sequence of *Pseudomonas aeruginosa* PA01, an opportunistic pathogen". *Nature*. vol. 406, Aug. 31, 2000, pp. 959-964.

European Search Report for European Application 03791242.5, mailed Jul. 25, 2006.

* cited by examiner

*Primary Examiner*—Anand U Desai
(74) *Attorney, Agent, or Firm*—Hamre, Schumann, Mueller & Larson, P.C.

(57) ABSTRACT

A process for producing glucose dehydrogenases. This process comprises transferring a DNA containing a sequence represented by SEQ ID NO:1 which encodes an α subunit having a glucose dehydrogenase activity and a β subunit being an electron transfer protein into a microorganism belonging to the genus *Pseudomonas* to thereby construct a transformant, and culturing this transformant so as to allow the production of a first glucose dehydrogenase containing the above-described β subunit and a second glucose dehydrogenase free from the β subunit. The α subunit as described above has a molecular weight of about 60 kDa measured by, for example, SDS-polyacrylamide gel electrophoresis under reducing conditions, while the β subunit as described above has a molecular weight of about 43 kDa measured by, for example, SDS-polyacrylamide gel electrophoresis under reducing conditions.

18 Claims, 1 Drawing Sheet

Lane 1: MARKER

Lane 2: FIRST PURIFIED ENZYME

Lane 3: SECOND PURIFIED ENZYME

PROCESS FOR PRODUCING GLUCOSE DEHYDROGENASES

TECHNICAL FIELD

The present invention relates to a process for producing glucose dehydrogenase. The glucose dehydrogenase that is obtained by this process can be suitably used in a glucose sensor.

BACKGROUND ART

Development of biosensors using enzymes that react specifically on specific substrates are actively under way regardless of the industrial field. A typical example of biosensors is the glucose sensor, which is mainly used in the medical field.

The glucose sensor serves to build a reaction system that contains an enzyme and an electron transmitter, and when using this glucose sensor, the glucose is quantitativley determined using, for example, the amperometric technique. Glucose oxidase (GOD) or glucose dehydrogenase (GDH) is used as the enzyme (Japanese Patent Application Laid-open No. 2002-65778).

Since GOD has high substrate specificity towards glucose and has excellent thermostability, massive production of the enzyme is possible, such that it has the advantage that the manufacturing cost is inexpensive compared to other enzymes. However, systems that use GOD have the problem that they are easily influenced by the oxygen that is dissolved in the measurement sample, such that the dissolved oxygen exerts an effect on the measurement results.

On the other hand, systems that use GDH are not easily influenced by the oxygen that is dissolved in the measurement sample. Therefore, systems that use GDH can measure glucose concentration with good accuracy even when carrying out measurements in an environment where oxygen partial pressure is low, or when measuring high concentration samples that require large quantities of oxygen. However, GDH has the problems that its thermostability is bad and its substrate specificity is worse than GOD.

From such circumstances, an enzyme that complements the shortcomings of both GOD and GDH was sought. SODE, who is one of the present inventors, isolated a new strain (*Burkholderia cepatia* KS1 strain) from a soil in the neighborhood of a thermal spring and obtained a novel GDH from this strain as disclosed in International Patent No. WO02/36779. This GDH consisted of α, β and γ subunits (hereinafter referred to as "CyGDH"), its reaction rate with the electron transmitter was high, and had no problem in regards to heat resistance, such that it was suitable as an enzyme for use in a glucose sensor.

However, since productivity of CyGDH was bad in the KS1 strain, massive production of CyGDH by the KS1 strain was difficult when considering an industrial application. When the present inventors therefore introduced the DNA coding for the α, β and γ subunits into *Escherichia coli* and expressed them, GDH was efficiently produced. However, this GDH consisted of the α, and γ subunits, which was missing the β subunit (hereinafter referred to as "αGDH"). As described, the total of α, β and γ subunits could not be expressed by the process of transforming *Escherichia coli*.

In addition, when the present inventors examined the characteristics of αGDH, αGDH was found to have a slower reaction rate with the electron transmitter compared to CyGDH, but higher heat resistance than CyGDH, and a smaller Km for glucose. That is to say, αGDH was identified to be as useful as CyGDH, as an enzyme for use in a glucose sensor.

In prior art, to prepare 2 species of enzyme that are useful in this way, it was necessary to carry out separately each of the acquisition of expression strain, culture and purification, which was disadvantageous from the perspective of manufacturing costs and efficiency.

DISCLOSURE OF THE INVENTION

An object of the present invention is to prepare efficiently 2 species of GDH, which may be applied in, for example, a glucose sensor and the like.

The process for preparing the glucose dehydrogenase pertaining to the present invention comprises introducing DNA containing the sequence described in SEQ ID NO.: 1 coding for the α subunit, which has a glucose dehydrogenase activity, and the β subunit, which is an electron-transfer protein, into a microorganism belonging to the genus *Pseudomonas* to obtain a transformant, and culturing this transformant to produce a first glucose dehydrogenase containing the β subunit and a second glucose dehydrogenase not containing the β subunit.

The α subunit has a molecular weight of approximately 60 kDa for example as determined by SDS-polyacrylamide gel electrophoresis under reducing conditions, is. On the other hand, the β subunit has a molecular weight of approximately 43 kDa for example as determined by SDS-polyacrylamide gel electrophoresis under reducing conditions.

The DNA may contain a base sequence coding for the γ subunit which has a molecular weight of approximately 14 kDa as determined by SDS-polyacrylamide gel electrophoresis under reducing conditions. In this case, the first and the second glucose dehydrogenase are produced as containing the γ subunit.

Examples of the microorganisms belonging to *Pseudomonas* include *Pseudomonas putida*, *Pseudomonas fluorescens*, *Pseudomonas aeruginosa* and the like; however, the use of *Pseudomonas putida* is preferred from the perspective of safety of the recombinant.

The DNA can be obtained from, for example, a microorganism that belongs to the genus *Burkholderia* that is capable of producing an enzyme having glucose dehydrogenase activity. The microorganism belonging to the genus *Burkholderia* adopted in the present invention is not limited in particular as long as it is a microorganism that belongs the genus *Burkholderia* and is capable of producing the present enzyme; however, *Burkholderia cepatia*, in particular the *Burkholderia cepatia* KS1 strain (hereinafter, simply referred to as the "KS1 strain") is preferred.

This KS1 strain is a new strain that SODE isolated from a soil in the nationhood of a thermal spring, and was identified as *Burkholderia cepatia* from its microbiological properties, and named KS1 strain. This KS1 strain was deposited at The National Institute of Advanced Industrial Science and Technology International Patent Organism Depositary (Chuo Dai-6, 1-1, Higashi 1-chome, Tsukuba-shi, Ibaraki-ken, 305-8566 Japan) as Microorganism Depository No. FERM BP-7306, on Sep. 25, 2000.

Note that when the present inventors measured glucose dehydrogenase activity in strains other than the KS1 strain by ordering a number of strains of the same *Burkholderia cepatia* that were deposited at the Institute for Fermentation, Osaka (IFO) or the Japan Collection of Microorganisms (JCM) of the Riken Institute of Physical and Chemical Research, they confirmed that the activity existed in all the strains. Therefore, *Burkholderia cepatia* other than the KS1 strain, for example, JCM5506, JCM5507, JCM2800, JCM2801, IFO15124 and IFO14595 can be adopted as the microorganism for obtaining the DNA used in the present invention.

The DNA is isolated from the chromosomal DNA of *Burkholderia cepatia*; however, since its base sequence and the amino acid sequence coded by the same base sequence are determined, it can also be obtained by chemically synthesis based on these sequences.

The amino acid sequence of SEQ ID NO.: 3, or an amino acid sequence wherein one or a plurality of amino acid residues have been substituted, deleted, intercalated or added in the amino acid sequence of SEQ ID NO.: 3, for example, is adopted as the α subunit. This α subunit is coded by, for example, the base sequence consisting of the bases No. 764 to 2380 among the base sequence of SEQ ID NO.: 1. Therefore, the use of a DNA having the above-mentioned base sequence is preferred as the DNA to be used in the present invention.

The amino acid sequence of SEQ ID NO.: 5, or an amino acid sequence wherein one or a plurality of amino acid residues have been substituted, deleted, intercalated or added in the amino acid sequence of SEQ ID NO.: 5, for example, is adopted as the β subunit. This β subunit is coded by, for example, the base sequence consisting of the bases No. 2386 to 3660 among the base sequence of SEQ ID NO.: 1. Therefore, the use of a DNA having the above-mentioned base sequence is preferred as the DNA to be used in the present invention.

It has been determined by SODE, that a high enzymatic activity is obtained when the γ subunit is expressed together with the α subunit compared to when the α subunit is expressed alone. Therefore, from the point of view of the enzymatic activity, it is preferred to express the γ subunit, and it is preferred that in the DNA, the base sequence coding for the γ subunit be contained in the upstream region of the base sequence coding for the α subunit. It can be thought that, in this way, when producing the α subunit, the α subunit can be efficiently produced inside the body of the microorganism by the fact that the γ subunit is first expressed and is present as a protein.

The amino acid sequence of SEQ ID NO.: 2, or an amino acid sequence wherein one or a plurality of amino acid residues have been substituted, deleted, intercalated or added in the amino acid sequence of SEQ ID NO.: 2, for example, is adopted as the γ subunit. This γ subunit is coded by, for example, the base sequence consisting of the bases No. 258 to 761 among the base sequence of SEQ ID NO.: 1. Therefore, the use of a DNA having the above-mentioned base sequence is preferred as the DNA to be used in the present invention.

Among the base sequence of SEQ ID NO.: 1, it is supposed that the base sequence beyond base No. 2386 is coding for the β subunit, and it is speculated that the base sequence from base No. 2386 to 2451 is coding for the signal peptide of the β subunit. The amino acid sequence derived from the same signal peptide is the amino acid sequence from amino acid No. 1 to 22 of SEQ ID NO.: 4.

As the signal peptide is a peptide that is required when a protein that has been synthesized by the ribosome passes through the inner membrane and is secreted in the periplasmic space, if the signal peptide is present, the quantity of protein contained in the periplasm of the cell or the culture supernatant is increased. Therefore, using a DNA containing the base sequence coding for the expression of the signal peptide of the β subunit as the DNA is preferred.

PREFERRED MODE FOR CARRYING OUT THE INVENTION

Hereinafter, the process for preparing the glucose dehydrogenase pertaining to the present invention will be described concretely.

A Step 1 of obtaining the DNA coding for the expression of for example the α subunit and the β subunit, a Step 2 of introducing a recombinant vector containing this DNA into a microorganism belonging to the genus *Pseudomonas* to create a transformant, a Step 3 of culturing this transformant in a culture medium to produce a glucose dehydrogenase that contains the β subunit (for example CyGDH) and a glucose dehydrogenase that does not contain the β subunit (for example αGDH), and a Step 4 of collecting the glucose dehydrogenase from the culture medium or the microorganism, are included in the present preparation process.

<Step 1 (Obtaining DNA)>

For obtaining the DNA, first, a recombinant vector is constructed. The recombinant vector is constructed, after isolating and purifying the chromosomal DNA from a microorganism belonging to the genus *Burkholderia* (for example *Burkholderia cepatia* KS1 strain), by linking and closing the chain between a chromosomal DNA fragment resulting from the cutting of this chromosomal DNA or a DNA fragment that was amplified by PCR and the like, and a linear expression vector.

Isolation and purification of the chromosomal DNA is carried out based on a bacterial lysate obtained from the bacteriolysis of microorganism. Example of bacteriolysis process include, for example, treatment by a bacteriolysis enzyme such as lysozyme, and in addition to this treatment, proteases, other enzymes and detergents such as sodium lauryl sulfate (SDS) are used in combination, as necessary. In addition, physically rupturing process such as freeze thawing and treatment with French press application can be used in combination. On the other hand, isolation and purification of DNA from the bacterial lysate can be carried out by suitably combining process such as, for example, protein-removal treatments such as phenol treatment and protease treatment, ribonuclease treatment, and alcohol precipitation treatment.

Cutting of the chromosomal DNA can be carried out according to process of the art, for example using sonication treatment and restriction endonuclease treatment. As for the restriction endonuclease, for example, the type II restriction endonuclease that acts on a specific nucleotidic sequence is used.

Linkage of the chromosomal DNA fragment and the expression vector is carried out, for example, using DNA ligase.

Expression vectors that may self multiply inside the host microorganism and have been constructed for gene recombination from a bacteriophage or a plasmid are suitable. Examples of bacteriophages include, for example, Lambda gt10, Lambda gt11 and the like, in case *Escherichia coli* described below is to be the host microorganism. On the other hand, examples of plastids include, for example, pBR322, pUC18, pUC118, pUC19, pUC119, pTrc99A, pBluescript or SuperCosI, which is a cosmid, and the like, in case *Escherichia coli* is to be the host microorganism. In addition, examples include RSF1010, pBBR122, pCN51 and the like, which are wide host range vectors for Gram-negative bacteria, in case *Pseudomonas* is to be used.

Next, a marker is provided to the recombinant vector, and a host microorganism is transfected with this recombinant vector to create a transformant. Screening is carried out with the expression of this vector marker and the enzymatic activity as the index, to obtain the gene donor microorganism, which retains the recombinant vector containing the gene coding for GDH, from this transformant.

The host microorganism is not limited as long as the recombinant vector is stable, and self-replicating and can express the character of an exogenous gene. Generally, *Escherichia coli* DH5α, XL-1 Blue MR and the like can be used. For example in case the host microorganism is *Escherichia coli*, the competent cell process by calcium treatment, electroporation process, and the like can be used as process for transfecting a host microorganism with a recombinant vector.

In addition, after the gene donor microorganism is cultured and the recombinant vector is isolated and purified from this microorganism, the gene coding for GDH (cloning fragment) is collected from the recombinant vector. Collection of the cloning fragment can be carried out by the same process as for collecting the chromosomal DNA.

This cloning fragment has a base sequence coding for the α subunit, which has the glucose dehydrogenase activity, and the β subunit, which is an electron-transfer protein. When obtaining the target DNA from the *Burkholderia cepatia* KS1 strain, the cloning fragment is obtained as one containing the base sequence coding for the γ subunit in addition to the base sequence coding for the α subunit and the β subunit (containing the signal peptide of the β subunit). Note that, the fact that the cloning fragment is coding for the α subunit and the β subunit, or the fact that it is coding for the γ subunit can be verified by decoding the base sequence of this cloning fragment by a process of the art.

<Step 2 (Creation of the Transformant)>

The transformant containing the target DNA is created by integrating the cloning fragment obtained in Step 1 into a vector, thereafter introducing the latter into a microorganism that belongs to the genus *Pseudomonas*. For example, *Pseudomonas putida* is used preferably as the microorganism that belongs to the genus *Pseudomonas*. The process for introducing a recombinant vector into a host microorganism can be carried out by the same process as for the creation of a transformant for the screening in Step 1.

<Step 3 (Culture of the Transformant and Production of GDH)>

The transformant obtained in Step 2 is cultured so as to make it produce GDH. GDH containing the β subunit and GDH not containing the β subunit are simultaneously produced from this transformant. For example, in case the target DNA has been obtained from the *Burkholderia cepatia* KS1 strain, CyGDH having the α, β and γ subunits and αGDH having the α and γ subunits are produced simultaneously.

As far as the format of the culture of the transformant is concerned, it suffices to select the culture conditions by considering the nutritional physiological character of the host, and liquid cultures are often carried out. Industrially, it is advantageous to carry out aerobic shaking cultures.

As far as the source of nutrient for the culture medium is concerned, those that are generally used in cultures of microorganism may be broadly used. As far as the carbon source is concerned, carbon compounds that can be assimilated are sufficient, and for example glucose, sucrose, lactose, maltose, molasses, pyruvic acid and the like are used. As for the nitrogen source, nitrogen compounds that can be assimilated are sufficient, for example peptone, meat extract, yeast extract, casein hydrolysate, soybean alkaline extract and the like are used. In addition, salts such as phosphate, carbonate, sulphate, magnesium, calcium, potassium, iron, manganese and zinc, specific amino acids, specific vitamins and the like are used as necessary.

The culture temperature may be suitably modified within a range where the transformant grows and the transformant produces GDH, and is preferably on the order of 20 to 42° C. It suffices that the culture completes at a suitable time by aiming for the time when GDH reaches maximum yield, and in general, culture time is on the order of 12 to 72 hours. The pH of the culture medium may be suitably modified within a range where the transformant developments and the transformant produces GDH, and preferably is in a range of on the order of pH 5.0 to 9.0.

<Step 4 (Collection of GDH)>

Collection of GDH is carried out, in general, after isolating a GDH-containing solution from the culture solution or the transformant following a process of the art, by purifying this GDH-containing solution.

In the case where GDH is present inside the cell, the GDH-containing solution can be obtained, after collecting the cells from the culture solution by means such as filtration or centrifugal separation and the like, by disrupting these cells by a mechanical process or an enzymatic process such as lysozyme and adding a chelating agent such as EDTA and a detergent as necessary, to solubilize GDH. On the other hand, in the case where GDH is present outside of the cell (in the culture solution), it can be obtained by separating the culture solution and the cell by means such as filtration or centrifugal separation.

Purification of the GDH-containing solution can be carried out directly from this solution, or can also be carried out after concentrating the GDH in this solution. The concentration can be carried out, for example by vacuum concentration, membrane concentration, salt precipitation treatment, or fractional precipitation process by a hydrophilic organic solvent (for example methanol, ethanol and acetone). Heat treatment and isoelectric point treatment are also effective purification means for the concentration of GDH. Purification of the concentrated solution can be carried out, for example, by suitably combining gel filtration, adsorption chromatography, ion exchange chromatography and affinity chromatography. Thereby, GDH containing the β subunit and GDH not containing the β subunit can be obtained separately.

The purified enzyme obtained in this way can be powderized, for example, by lyophilization, vacuum drying and spray drying, and circulated in the market.

EXAMPLE

In the following, concrete examples of the preparation process described above will be described while the fact that 2 species of GDH are obtained will be demonstrated through this example.

<Preparation of Chromosomal DNA from the *Burkholderia cepatia* KS1 Strain>

The chromosomal DNA from the *Burkholderia cepatia* KS1 strain was prepared following a process of the art. That is to say, first, the KS1 strain was agitated overnight at 34° C., using the TL liquid medium (polypeptone=10 g, yeast extract=1 g, NaCl=5 g, $KH_2PO_4$=2 g, glucose=5 g; 1 L total volume, pH 7.2). The grown cells were recovered with a centrifuge. These cells were suspended in a solution containing 10 mM NaCl, 20 mM Tris-HCl (pH8.0), 1 mMEDTA, 0.5% SDS, and 100 μg/mL proteinase K, and treated for 6 hours at 50° C. After the same quantity of phenol-chloroform was added to this suspension and agitated for 10 minutes at room temperature, the supernatant was recovered with a centrifuge. Sodium acetate was added thereto so as to obtain a final concentration of 0.3M, twice the amount of ethanol was overlaid to precipitate the chromosomal DNA at the middle layer. After the precipitate was fished out using a glass rod and washed with 70% ethanol, it was dissolved in an appropriate amount of TE buffer, to obtain a chromosomal DNA solution.

<Creation of the Transformant>

The full length of the Gene coding for GDH was amplified by the PCR process with the previously obtained chromosomal DNA as the template. The sequence of the N-terminal portion of the GDH γ subunit and the sequence of the C-terminal portion of the GDH β subunit were used as primers. After a fragment resulting from the cut of this DNA fragment at the restriction endonuclease recognition site located at the ends of each primer, and a DNA fragment containing the trc promoter were prepared and linked to the wide host range vector RSF1010, the vector was introduced into *Escherichia coli* JM109, to form a colony on an LB agar medium containing 50 μg/ml streptomycin. A plasmid was prepared from the colony that developed, with this as the template and using the previously described PCR primer, a clone for which a fragment of approximately 3.4 Kb is amplified by PCR was selected, which was introduced in the *Pseudomonas putida* ATCC47054 strain, to obtain the target transformant (GDH expressing strain).

<Culture of the Transformant and Generation Production of GDH>

The culture of the transformant was carried out under aerobic culture conditions. More specifically, the culture of the transformant was carried out for 8 hours at 34° C., using 7 L of a culture medium that was adjusted so as to have a composition per liter of culture solution of Table 1. Cells were obtained by centrifuging 7 L of the present culture solution at 9,000×g (4° C., 10 minutes).

TABLE 1

COMPOSITION OF CULTURE MEDIUM

| Polypeptone | 10 g |
| Yeast extract | 1 g |
| NaCl | 5 g |
| $KH_2PO_4$ | 2 g |
| Glucose | 5 g |
| Einol (ABLECo. TokyoJapan) | 0.14 g |
| Total, distilled water | 1 L |
| pH adjustment | 7.2 |

<Purification of GDH>

The cells that were obtained were disrupted, while in a dispersed state in 10 mM potassium phosphate buffer solution (pH6.0), by applying a pressure difference of 1,500 Kg/cm$^2$ with a French press (Otake Seisakusyo Co., Ltd., Tokyo, Japan). The cell extract that was obtained at this time was centrifuged for 10 minutes at 8,000×g, and a crude enzyme solution devoid of cell solids was obtained.

Triton-X100 was added to the crude enzyme solution so as to obtain a final concentration of 1%. Next, the solution was agitated slowly overnight at 4° C. Then, after ultracentrifugation (4° C., 69800×g, 90 minutes), it was re-centrifuged (4° C., 15000×g, 15 minute), and the solubilized fraction was obtained as the supernatant.

After this solubilized fraction was dialyzed against a 10 mM potassium phosphate buffer solution (pH8.0) containing 0.2% Triton-X100, this solution was supplied to a Q-Sepharose FF column (22 mm ID×20 cm Amersham Bioscience), which was equilibrated with a 10 mM potassium phosphate buffer solution (pH8.0) containing 0.2% Triton-X100. The protein was eluted with a linear gradient such that the concentration of NaCl in the 10 mM potassium phosphate buffer solution (pH8.0) goes from 0 to 500 mM. The elution was carried out at a flow rate of 5 mL/min.

Figure 1:
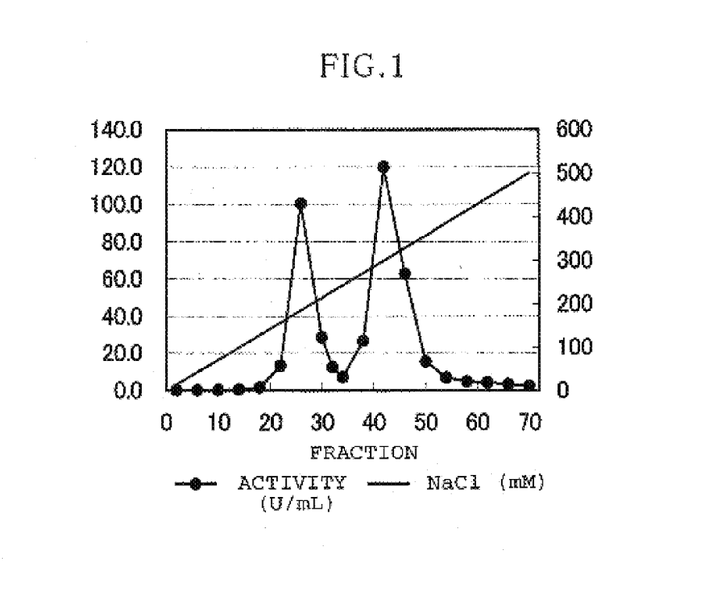
FIG. 1 shows the results of Q-Sepharose FF chromatography of a soluble fraction obtained from a transformant.

In regard to the eluate, GDH activity was measured for each fraction. The result is represented schematically in FIG. 1. As can be understood from FIG. 1, two large peaks were identified within the range where the gradient was applied.

Measurement of GDH activity was carried out by following the reaction of reduction of the electron acceptor, which is based on the dehydrogenation of glucose. 2,6-dichlorophenolindophenol (DCIP) and phenazine methosulfate (PMS) were used as electron acceptors. The reaction was carried out in a polyethylene tube at a prescribed temperature.

First, 5 μL of enzyme solution was added to 20 μL of 25 mM tris-hydroxymethyl-aminomethane HCl buffer solution (pH8.0) containing 0.75 mM PMS and 0.75 mM DCIP to prepare a mix solution. Beforehand, this mix solution was let to stand at a constant temperature for 1 minute. The reaction was started by adding 1 μL of 2M glucose (final concentration: 77 mM) to the mix solution, which was let to stand for 2 minutes at constant temperature. Next, 100 μL of ice-cold distilled water or 120 μL of 7.5M urea was added to cool the sample. For this sample, bleaching based on DCIP reduction was measured chronologically using an ultramicro measurement cell (100 μL) and a spectrophotometer that can perform measurements using this cell (UV160, Shimadzu, Kyoto. Japan). The measurement wavelength was set to 600 nm, the absorption wavelength of DCIP. The molar extinction coefficient of DCIP was 22.23 mM×cm$^{-1}$. One enzyme unit (U) was defined as the quantity that oxidizes 1 μM glucose per minute under standard assay conditions. The protein concentration was measured with Lowry's process.

Next, fractions were collected separately for the two GDH activity peaks, dialyzed overnight with a 10 mM potassium phosphate buffer solution (pH8.0, 4° C.) containing 0.2% Triton-X100, and 2 species of GDH solution were prepared.

Each GDH preparation solution was purified separately using a DEAE-5PW column (8.0 mm ID×7.5 cm Toso, Tokyo, Japan). The column was pre-equilibrated with a 10 mM potassium phosphate buffer solution (pH8.0) containing 0.2% Triton-X100 The protein was eluted at a flow rate of 1 mL/min with a linear gradient such that the concentration of NaCl in the 10 mM potassium phosphate buffer solution (pH8.0) went from 0 to 400 mM. For each chromatography, the fractions with the highest GDH activity were collected, desalted overnight with a 10 mM potassium phosphate buffer solution (pH8.0) containing 0.2% Triton-X100, and 2 species of purified enzyme (hereinafter referred to as "first purified enzyme" and "second purified enzyme" for convenience) were obtained.

<Determination of the Subunits of the Purified Enzymes>

Each purified enzyme solution was subjected to electrophoresis by SDS-PAGE, and the molecular weights of the subunits were determined. The SDS-PAGE was carried out in an 8-25% polyacrylamide gradient gel using a Tris-Tricine buffer solution. The proteins on the gel were subjected to coomassie staining. Separation and development were carried out automatically with the Phast System (Pharmacia). The molecular mass was measured by the relative mobility of standard proteins.

Figure 2:
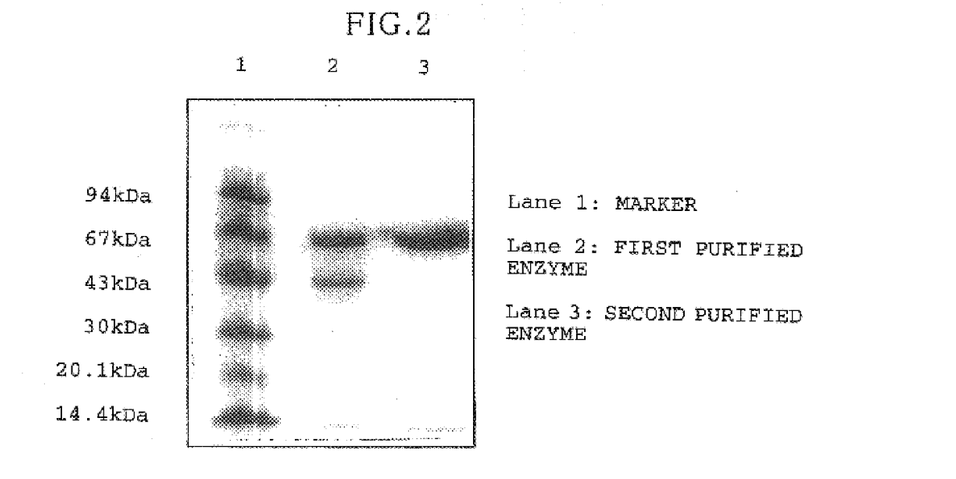
FIG. 2 shows the results of SDS-PAGE.

The results from the SDS-PAGE electrophoresis are shown in FIG. 2. In FIG. 2 are respectively shown the coomassie staining of standard molecular weight marker proteins in lane 1, the coomassie staining of the first purified enzyme in lane 2, and the coomassie staining of the second purified enzyme in lane 3. As can be understood from the same Fig., the first purified enzyme was divided into proteins whose the molecular weight are approximately 60 kDa, approximately 43 kDa and approximately 14 kDa. Therefore, it is suggested that the α subunit with a molecular weight of approximately 60 kDa, the β subunit with a molecular weight of approximately 43 kDa, and the γ subunit with a molecular weight of approximately 14 kDa are bound in the first purified enzyme. The second purified enzyme was divided into proteins whose molecular weight are approximately 60 kDa and approximately 14 kDa. Therefore, it is suggested that the α subunit with a molecular weight of approximately 60 kDa and the γ subunit with a molecular weight of approximately 14 kDa are bound in the second purified enzyme. The results of the SDS-PAGE electrophoresis show that the first purified enzyme and the second purified enzyme are different GDH, and that 2 species of GDH were simultaneously generated.

After the bands containing the α subunit and the β subunit by electrophoresis were respectively cut out and transferred onto poly vinylidene fluorid membranes, the amino acid sequence was analyzed with an amino acid sequencer (Shimadzu, PPSQ-10).

For the α subunit, it was determined that it contained a peptide sequence of 11 residue consisting of the amino acid No. 2 to 12 in the amino acid sequence of SEQ ID NO.: 3. On the other hand, for the β subunit, it was possible to identify an amino acid sequence of 16 residues at the N-terminus, shown in SEQ ID NO.: 5.

<Analysis of the Recombinant Vector>

The target recombinant vector was extracted from the transformants of *Pseudomonas putida* having GDH activity. The base sequence of the inserted DNA fragment of this recombinant vector was determined by a process of the art. The result showed that it contained the base sequence of SEQ ID NO.: 258 to 3660.

As disclosed in International Patent Publication No. WO02/36779 and the like, the base sequence coding for the α subunit is the base sequence of base No. 764 to 2380 among the base sequence of SEQ ID NO.: 1, the base sequence coding for the β subunit is the base sequence of base No. 2386 to 3660 among SEQ ID NO.: 1, the base sequence coding for the γ subunit is the base sequence of base No. 258 to 761 among the base sequence of SEQ ID NO.: 1, and the base sequence coding for the signal peptide of the β subunit is the base sequence of base No. 2386 to 2451 among the base sequence of SEQ ID NO.: 1.

Therefore, it was verified that the target recombinant vector contains a base sequence coding for the α subunit, the β subunit (containing the signal peptide of the β subunit) and the γ subunit. Note that the amino acid sequence corresponding to each base sequence is shown in SEQ ID NO.: 3 for the α subunit, SEQ ID NO.: 5 for the β subunit, SEQ ID NO.: 2 for the γ subunit, and amino acids No. 1 to 22 among the amino acid sequence of SEQ ID NO.: 4 for the signal peptide of the β subunit.

As can be understood from the foregoing, in the present invention, it is possible to produce simultaneously, moreover, efficiently, 2 species of GDH, such as, for example, αGDH and CyGDH.

The invention claimed is:

1. A process for preparing glucose dehydrogenase, comprising:

introducing DNA containing the sequence described in SEQ ID NO: 1 coding for an α subunit, which has a glucose dehydrogenase activity, and a β subunit, which is an electron-transfer protein, into a microorganism belonging to the genus *Pseudomonas* to obtain in a transformant, and culturing this transformant to produce a first glucose dehydrogenase containing said β subunit and a second glucose dehydrogenase not containing said β subunit.

2. The process for preparing glucose dehydrogenase as recited in claim 1, wherein said α subunit has a molecular weight of approximately 60 kDa as determined by SDS-polyacrylamide gel electrophoresis under reducing conditions; and said β subunit has a molecular weight of approximately 43 kDa as determined by SDS-polyacrylamide gel electrophoresis under reducing conditions.

3. The process for preparing glucose dehydrogenase as recited in claim 1, wherein said DNA contains a base sequence coding for a γ subunit which has a molecular weight of approximately 14 kDa as determined by SDS-polyacrylamide gel electrophoresis under reducing conditions; and said first and second glucose dehydrogenase are produced as containing said γ subunit.

4. The process for preparing glucose dehydrogenase as recited in claim 1, wherein said DNA is obtained from a microorganism belonging to the genus *Burkholderia* and capable of producing an enzyme having glucose dehydrogenase activity.

5. The process for preparing glucose dehydrogenase as recited in claim 4, wherein said microorganism belonging to the genus *Burkholderia* is the *Burkholderia cepatia* KS1 strain (FERN BP-7306).

6. The process for preparing glucose dehydrogenase as recited in claim 1, wherein said α subunit has an amino acid sequence which is the amino acid sequence of SEQ ID NO: 3.

7. The process for preparing glucose dehydrogenase as recited in claim 6, wherein said DNA contains a base sequence coding for the α subunit consisting of base Nos. 764 to 2380 among the base sequence of SEQ ID NO: 1.

8. The process for preparing glucose dehydrogenase as recited in claim 1, wherein said β subunit has an amino acid sequence which is the amino acid sequence of SEQ ID NO: 5.

9. The process for preparing glucose dehydrogenase as recited in claim 8, wherein said DNA contains a base sequence coding for the β subunit consisting of base Nos. 2386 to 3660 among SEQ ID NO: 1.

10. The process for preparing glucose dehydrogenase as recited in claim 3, wherein said γ subunit is the amino acid sequence of SEQ ID NO: 2.

11. The process for preparing glucose dehydrogenase as recited in claim 10, wherein said DNA contains a base sequence coding for the γ subunit consisting of base Nos. 258 to 761 among the base sequence of SEQ ID NO: 1.

12. The process for preparing glucose dehydrogenase as recited in claim 11, wherein said DNA contains a base sequence coding for the γ subunit in a region that is more upstream than the base sequence coding for the α subunit.

13. The process for preparing glucose dehydrogenase as recited in claim 1, wherein said DNA contains a base sequence coding for a signal peptide of said β subunit.

14. The process for preparing glucose dehydrogenase as recited in claim 13, wherein said signal peptide has the amino acid sequence of amino acids Nos. 1 to 22 among the amino acid sequence of SEQ ID NO: 4.

15. The process for preparing glucose dehydrogenase as recited in claim 13, wherein said signal peptide is coded by the base sequence of base Nos. 2386 to 2451 among the base sequence of SEQ ID NO: 1.

16. A process for preparing glucose dehydrogenase, comprising:
introducing DNA containing the sequence described in SEQ ID NO: 1 coding for an α subunit, which has a glucose dehydrogenase activity, and a β subunit, which is an electron-transfer protein, into a microorganism belonging to the genus *Pseudomonas* to obtain in a transformant, and culturing this transformant to produce a first glucose dehydrogenase containing said β subunit and a second glucose dehydrogenase not containing said β subunit,
wherein said microorganism belonging to *Pseudomonas* is *Pseudomonas putida*.

17. The process for preparing glucose dehydrogenase as recited in claim 16, wherein said DNA is obtained from a microorganism belonging to the genus *Burkholderia* and capable of producing an enzyme having glucose dehydrogenase activity.

18. The process for preparing glucose dehydrogenase as recited in claim 17, wherein said microorganism belonging to the genus *Burkholderia* is the *Burkholderia cepatia* KS1 strain (FERN BP-7306).

* * * * *

```
                        SEQUENCE LISTING

<160> NUMBER OF SEQ ID NOS: 5

<210> SEQ ID NO 1
<211> LENGTH: 3706
<212> TYPE: DNA
<213> ORGANISM: Burkholderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(3660)

<400> SEQUENCE: 1
aagctttctg tttgattgca cgcgattcta accgagcgtc tgtgaggcgg aacgcgacat     60
gcttcgtgtc gcacacgtgt cgcgccgacg acacaaaaat gcagcgaaat ggctgatcgt    120
tacgaatggc tgacacattg aatggactat aaaaccattg tccgttccgg aatgtgcgcg    180
tacatttcag gtccgcgccg attttgaga  aatatcaagc gtggttttcc cgaatccggt    240
gttcgagaga aggaaac atg cac aac gac aac act ccc cac tcg cgt cgc      290
                   Met His Asn Asp Asn Thr Pro His Ser Arg Arg
                    1               5                  10 cac ggc gac gca gcc gca tca ggc atc acg cgg cgt caa tgg ttg caa     338
His Gly Asp Ala Ala Ala Ser Gly Ile Thr Arg Arg Gln Trp Leu Gln
             15                  20                  25
```

-continued

| | | |
|---|---|---|
| ggc gcg ctg gcg ctg acc gca gcg ggc ctc acg ggt tcg ctg aca ttg<br>Gly Ala Leu Ala Leu Thr Ala Ala Gly Leu Thr Gly Ser Leu Thr Leu<br>30                           35                      40 | 386 |
| cgg gcg ctt gca gac aac ccc ggc act gcg ccg ctc gat acg ttc atg<br>Arg Ala Leu Ala Asp Asn Pro Gly Thr Ala Pro Leu Asp Thr Phe Met<br>45                          50                        55 | 434 |
| acg ctt tcc gaa tcg ctg acc ggc aag aaa ggg ctc agc cgc gtg atc<br>Thr Leu Ser Glu Ser Leu Thr Gly Lys Lys Gly Leu Ser Arg Val Ile<br>60                         65                        70                    75 | 482 |
| ggc gag cgc ctg ctg cag gcg ctg cag aag ggc tcg ttc aag acg gcc<br>Gly Glu Arg Leu Leu Gln Ala Leu Gln Lys Gly Ser Phe Lys Thr Ala<br>                  80                        85                        90 | 530 |
| gac agc ctg ccg cag ctc gcc ggc gcg ctc gcg tcc ggt tcg ctg acg<br>Asp Ser Leu Pro Gln Leu Ala Gly Ala Leu Ala Ser Gly Ser Leu Thr<br>                        95                       100                    105 | 578 |
| cct gaa cag gaa tcg ctc gca ctg acg atc ctc gag gcc tgg tat ctc<br>Pro Glu Gln Glu Ser Leu Ala Leu Thr Ile Leu Glu Ala Trp Tyr Leu<br>                    110                    115                    120 | 626 |
| ggc atc gtc gac aac gtc gtg att acg tac gag gaa gca tta atg ttc<br>Gly Ile Val Asp Asn Val Val Ile Thr Tyr Glu Glu Ala Leu Met Phe<br>125                        130                    135 | 674 |
| ggc gtc gtg tcc gat acg ctc gtg atc cgt tcg tat tgc ccc aac aaa<br>Gly Val Val Ser Asp Thr Leu Val Ile Arg Ser Tyr Cys Pro Asn Lys<br>140                        145                    150                    155 | 722 |
| ccc ggc ttc tgg gcc gac aaa ccg atc gag agg caa gcc tg atg gcc<br>Pro Gly Phe Trp Ala Asp Lys Pro Ile Glu Arg Gln Ala    Met Ala<br>                    160                    165                    170 | 769 |
| gat acc gat acg caa aag gcc gac gtc gtc gtc gtt gga tcg ggt gtc<br>Asp Thr Asp Thr Gln Lys Ala Asp Val Val Val Val Gly Ser Gly Val<br>                    175                    180                    185 | 817 |
| gcg ggc gcg atc gtc gcg cat cag ctc gcg atg gcg ggc aag gcg gtg<br>Ala Gly Ala Ile Val Ala His Gln Leu Ala Met Ala Gly Lys Ala Val<br>                        190                    195                    200 | 865 |
| atc ctg ctc gaa gcg ggc ccg cgc atg ccg cgc tgg gaa atc gtc gag<br>Ile Leu Leu Glu Ala Gly Pro Arg Met Pro Arg Trp Glu Ile Val Glu<br>205                        210                    215 | 913 |
| cgc ttc cgc aat cag ccc gac aag atg gac ttc atg gcg ccg tac ccg<br>Arg Phe Arg Asn Gln Pro Asp Lys Met Asp Phe Met Ala Pro Tyr Pro<br>220                        225                    230 | 961 |
| tcg agc ccc tgg gcg ccg cat ccc gag tac ggc ccg ccg aac gac tac<br>Ser Ser Pro Trp Ala Pro His Pro Glu Tyr Gly Pro Pro Asn Asp Tyr<br>235                        240                    245                    250 | 1009 |
| ctg atc ctg aag ggc gag cac aag ttc aac tcg cag tac atc cgc gcg<br>Leu Ile Leu Lys Gly Glu His Lys Phe Asn Ser Gln Tyr Ile Arg Ala<br>                        255                    260                    265 | 1057 |
| gtg ggc ggc acg acg tgg cac tgg gcc gcg tcg gcg tgg cgc ttc att<br>Val Gly Gly Thr Thr Trp His Trp Ala Ala Ser Ala Trp Arg Phe Ile<br>                        270                    275                    280 | 1105 |
| ccg aac gac ttc aag atg aag agc gtg tac ggc gtc ggc cgc gac tgg<br>Pro Asn Asp Phe Lys Met Lys Ser Val Tyr Gly Val Gly Arg Asp Trp<br>                    285                    290                    295 | 1153 |
| ccg atc cag tac gac gat ctc gag ccg tac tat cag cgc gcg gag gaa<br>Pro Ile Gln Tyr Asp Asp Leu Glu Pro Tyr Tyr Gln Arg Ala Glu Glu<br>300                        305                    310 | 1201 |
| gag ctc ggc gtg tgg ggc ccg ggc ccc gag gaa gat ctg tac tcg ccg<br>Glu Leu Gly Val Trp Gly Pro Gly Pro Glu Glu Asp Leu Tyr Ser Pro<br>315                        320                    325                    330 | 1249 |
| cgc aag cag ccg tat ccg atg ccg ccg ctg ccg ttg tcg ttc aac gag<br>Arg Lys Gln Pro Tyr Pro Met Pro Pro Leu Pro Leu Ser Phe Asn Glu<br>                        335                    340                    345 | 1297 |

```
                                                                -continued cag acc atc aag acg gcg ctg aac aac tac gat ccg aag ttc cat gtc    1345
Gln Thr Ile Lys Thr Ala Leu Asn Asn Tyr Asp Pro Lys Phe His Val
        350                 355                 360 gtg acc gag ccg gtc gcg cgc aac agc cgc ccg tac gac ggc cgc ccg    1393
Val Thr Glu Pro Val Ala Arg Asn Ser Arg Pro Tyr Asp Gly Arg Pro
                365                 370                 375 act tgt tgc ggc aac aac aac tgc atg ccg atc tgc ccg atc ggc gcg    1441
Thr Cys Cys Gly Asn Asn Asn Cys Met Pro Ile Cys Pro Ile Gly Ala
    380                 385                 390 atg tac aac ggc atc gtg cac gtc gag aag gcc gaa cgc gcc ggc gcg    1489
Met Tyr Asn Gly Ile Val His Val Glu Lys Ala Glu Arg Ala Gly Ala
395                 400                 405                 410 aag ctg atc gag aac gcg gtc gtc tac aag ctc gag acg ggc ccg gac    1537
Lys Leu Ile Glu Asn Ala Val Val Tyr Lys Leu Glu Thr Gly Pro Asp
                415                 420                 425 aag cgc atc gtc gcg gcg ctc tac aag gac aag acg ggc gcc gag cat    1585
Lys Arg Ile Val Ala Ala Leu Tyr Lys Asp Lys Thr Gly Ala Glu His
        430                 435                 440 cgc gtc gaa ggc aag tat ttc gtg ctc gcc gcg aac ggc atc gag acg    1633
Arg Val Glu Gly Lys Tyr Phe Val Leu Ala Ala Asn Gly Ile Glu Thr
                445                 450                 455 ccg aag atc ctg ctg atg tcc gcg aac cgc gat ttc ccg aac ggt gtc    1681
Pro Lys Ile Leu Leu Met Ser Ala Asn Arg Asp Phe Pro Asn Gly Val
    460                 465                 470 gcg aac agc tcg gac atg gtc ggc cgc aac ctg atg gac cat ccg ggc    1729
Ala Asn Ser Ser Asp Met Val Gly Arg Asn Leu Met Asp His Pro Gly
475                 480                 485                 490 acc ggc gtg tcg ttc tat gcg agc gag aag ctg tgg ccg ggc cgc ggc    1777
Thr Gly Val Ser Phe Tyr Ala Ser Glu Lys Leu Trp Pro Gly Arg Gly
                495                 500                 505 ccg cag gag atg acg tcg ctg atc ggt ttc cgc gac ggt ccg ttc cgc    1825
Pro Gln Glu Met Thr Ser Leu Ile Gly Phe Arg Asp Gly Pro Phe Arg
        510                 515                 520 gcg acc gaa gcg gcg aag aag atc cac ctg tcg aac ctg tcg cgc atc    1873
Ala Thr Glu Ala Ala Lys Lys Ile His Leu Ser Asn Leu Ser Arg Ile
                525                 530                 535 gac cag gag acg cag aag atc ttc aag gcc ggc aag ctg atg aag ccc    1921
Asp Gln Glu Thr Gln Lys Ile Phe Lys Ala Gly Lys Leu Met Lys Pro
    540                 545                 550 gac gag ctc gac gcg cag atc cgc gac cgt tcc gca cgc tac gtg cag    1969
Asp Glu Leu Asp Ala Gln Ile Arg Asp Arg Ser Ala Arg Tyr Val Gln
555                 560                 565                 570 ttc gac tgc ttc cac gaa atc ctg ccg caa ccc gag aac cgc atc gtg    2017
Phe Asp Cys Phe His Glu Ile Leu Pro Gln Pro Glu Asn Arg Ile Val
                575                 580                 585 ccg agc aag acg gcg acc gat gcg atc ggc att ccg cgc ccc gag atc    2065
Pro Ser Lys Thr Ala Thr Asp Ala Ile Gly Ile Pro Arg Pro Glu Ile
        590                 595                 600 acg tat gcg atc gac gac tac gtg aag cgc ggc gcc gcg cat acg cgc    2113
Thr Tyr Ala Ile Asp Asp Tyr Val Lys Arg Gly Ala Ala His Thr Arg
                605                 610                 615 gag gtc tac gcg acc gcc gcg aag gtg ctc ggc ggc acg gac gtc gtg    2161
Glu Val Tyr Ala Thr Ala Ala Lys Val Leu Gly Gly Thr Asp Val Val
    620                 625                 630 ttc aac gac gaa ttc gcg ccg aac aat cac atc acg ggc tcg acg atc    2209
Phe Asn Asp Glu Phe Ala Pro Asn Asn His Ile Thr Gly Ser Thr Ile
635                 640                 645                 650 atg ggc gcc gat gcg cgc gac tcc gtc gtc gac aag gac tgc cgc acg    2257
Met Gly Ala Asp Ala Arg Asp Ser Val Val Asp Lys Asp Cys Arg Thr
```

-continued

```
                       655                 660                 665
ttc gac cat ccg aac ctg ttc att tcg agc agc gcg acg atg ccg acc              2305
Phe Asp His Pro Asn Leu Phe Ile Ser Ser Ser Ala Thr Met Pro Thr
            670                 675                 680 gtc ggt acc gta aac gtg acg ctg acg atc gcc gcg ctc gcg ctg cgg              2353
Val Gly Thr Val Asn Val Thr Leu Thr Ile Ala Ala Leu Ala Leu Arg
                685                 690                 695 atg tcg gac acg ctg aag aag gaa gtc tgacc gtg cgg aaa tct act ctc            2403
Met Ser Asp Thr Leu Lys Lys Glu Val     Val Arg Lys Ser Thr Leu
    700                 705                     710 act ttc ctc atc gcc ggc tgc ctc gcg ttg ccg ggc ttc gcg cgc gcg              2451
Thr Phe Leu Ile Ala Gly Cys Leu Ala Leu Pro Gly Phe Ala Arg Ala
        715                 720                 725 gcc gat gcg gcc gat ccg gcg ctg gtc aag cgc ggc gaa tac ctc gcg              2499
Ala Asp Ala Ala Asp Pro Ala Leu Val Lys Arg Gly Glu Tyr Leu Ala
730                 735                 740                 745 acc gcc atg ccg gta ccg atg ctc ggc aag atc tac acg agc aac atc              2547
Thr Ala Met Pro Val Pro Met Leu Gly Lys Ile Tyr Thr Ser Asn Ile
                750                 755                 760 acg ccc gat ccc gat acg ggc gac tgc atg gcc tgc cac acc gtg aag              2595
Thr Pro Asp Pro Asp Thr Gly Asp Cys Met Ala Cys His Thr Val Lys
            765                 770                 775 ggc ggc aag ccg tac gcg ggc ggc ctt ggc ggc atc ggc aaa tgg acg              2643
Gly Gly Lys Pro Tyr Ala Gly Gly Leu Gly Gly Ile Gly Lys Trp Thr
        780                 785                 790 ttc gag gac ttc gag cgc gcg gtg cgg cac ggc gtg tcg aag aac ggc              2691
Phe Glu Asp Phe Glu Arg Ala Val Arg His Gly Val Ser Lys Asn Gly
    795                 800                 805 gac aac ctg tat ccg gcg atg ccg tac gtg tcg tac gcg aag atc aag              2739
Asp Asn Leu Tyr Pro Ala Met Pro Tyr Val Ser Tyr Ala Lys Ile Lys
810                 815                 820                 825 gac gac gac gta cgc gcg ctg tac gcc tac ttc atg cac ggc gtc gag              2787
Asp Asp Asp Val Arg Ala Leu Tyr Ala Tyr Phe Met His Gly Val Glu
                830                 835                 840 ccg gtc aag cag gcg ccg ccg aag aac gag atc cca gcg ctg cta agc              2835
Pro Val Lys Gln Ala Pro Pro Lys Asn Glu Ile Pro Ala Leu Leu Ser
            845                 850                 855 atg cgc tgg ccg ctg aag atc tgg aac tgg ctg ttc ctg aag gac ggc              2883
Met Arg Trp Pro Leu Lys Ile Trp Asn Trp Leu Phe Leu Lys Asp Gly
        860                 865                 870 ccg tac cag ccg aag ccg tcg cag agc gcc gaa tgg aat cgc ggc gcg              2931
Pro Tyr Gln Pro Lys Pro Ser Gln Ser Ala Glu Trp Asn Arg Gly Ala
    875                 880                 885 tat ctg gtg cag ggt ctc gcg cac tgc agc acg tgc cac acg ccg cgc              2979
Tyr Leu Val Gln Gly Leu Ala His Cys Ser Thr Cys His Thr Pro Arg
890                 895                 900                 905 ggc atc gcg atg cag gag aag tcg ctc gac gaa acc ggc ggc agc ttc              3027
Gly Ile Ala Met Gln Glu Lys Ser Leu Asp Glu Thr Gly Gly Ser Phe
                910                 915                 920 ctc gcg ggg tcg gtg ctc gcc ggc tgg gac ggc tac aac atc acg tcg              3075
Leu Ala Gly Ser Val Leu Ala Gly Trp Asp Gly Tyr Asn Ile Thr Ser
            925                 930                 935 gac ccg aat gcg ggg atc ggc agc tgg acg cag cag cag ctc gtg cag              3123
Asp Pro Asn Ala Gly Ile Gly Ser Trp Thr Gln Gln Gln Leu Val Gln
        940                 945                 950 tat ttg cgc acc ggc agc gtg ccg ggc gtc gcg cag gcg gcc ggg ccg              3171
Tyr Leu Arg Thr Gly Ser Val Pro Gly Val Ala Gln Ala Ala Gly Pro
    955                 960                 965 atg gcc gag gcg gtc gag cac agc ttc tcg aag atg acc gaa gcg gac              3219
```

```
                                                                          -continued Met Ala Glu Ala Val Glu His Ser Phe Ser Lys Met Thr Glu Ala Asp
970                 975                 980                 985 atc ggt gcg atc gcc acg tac gtc cgc acg gtg ccg gcc gtt gcc gac       3267
Ile Gly Ala Ile Ala Thr Tyr Val Arg Thr Val Pro Ala Val Ala Asp
                990                 995                1000 agc aac gcg aag cag ccg cgg tcg tcg tgg ggc aag ccg gcc gag gac       3315
Ser Asn Ala Lys Gln Pro Arg Ser Ser Trp Gly Lys Pro Ala Glu Asp
            1005                1010                1015 ggg ctg aag ctg cgc ggt gtc gcg ctc gcg tcg tcg ggc atc gat ccg       3363
Gly Leu Lys Leu Arg Gly Val Ala Leu Ala Ser Ser Gly Ile Asp Pro
        1020                1025                1030 gcg cgg ctg tat ctc ggc aac tgc gcg acg tgc cac cag atg cag ggc       3411
Ala Arg Leu Tyr Leu Gly Asn Cys Ala Thr Cys His Gln Met Gln Gly
    1035                1040                1045 aag ggc acg ccg gac ggc tat tac ccg tcg ctg ttc cac aac tcc acc       3459
Lys Gly Thr Pro Asp Gly Tyr Tyr Pro Ser Leu Phe His Asn Ser Thr
1050                1055                1060                1065 gtc ggc gcg tcg aat ccg tcg aac ctc gtg cag gtg atc ctg aac ggc       3507
Val Gly Ala Ser Asn Pro Ser Asn Leu Val Gln Val Ile Leu Asn Gly
                1070                1075                1080 gtg cag cgc aag atc ggc agc gag gat atc ggg atg ccc gct ttc cgc       3555
Val Gln Arg Lys Ile Gly Ser Glu Asp Ile Gly Met Pro Ala Phe Arg
            1085                1090                1095 tac gat ctg aac gac gcg cag atc gcc gcg ctg acg aac tac gtg acc       3603
Tyr Asp Leu Asn Asp Ala Gln Ile Ala Ala Leu Thr Asn Tyr Val Thr
        1100                1105                1110 gcg cag ttc ggc aat ccg gcg gcg aag gtg acg gag cag gac gtc gcg       3651
Ala Gln Phe Gly Asn Pro Ala Ala Lys Val Thr Glu Gln Asp Val Ala
    1115                1120                1125 aag ctg cgc tga catagtcggg cgcgccgaca cggcgcaacc gataggacag gag       3706
Lys Leu Arg
1130

<210> SEQ ID NO 2
<211> LENGTH: 168
<212> TYPE: PRT
<213> ORGANISM: Pseudomonas putida

<400> SEQUENCE: 2

Met His Asn Asp Asn Thr Pro His Ser Arg Arg His Gly Asp Ala Ala
1               5                   10                  15

Ala Ser Gly Ile Thr Arg Arg Gln Trp Leu Gln Gly Ala Leu Ala Leu
            20                  25                  30

Thr Ala Ala Gly Leu Thr Gly Ser Leu Thr Leu Arg Ala Leu Ala Asp
        35                  40                  45

Asn Pro Gly Thr Ala Pro Leu Asp Thr Phe Met Thr Leu Ser Glu Ser
    50                  55                  60

Leu Thr Gly Lys Lys Gly Leu Ser Arg Val Ile Gly Glu Arg Leu Leu
65                  70                  75                  80

Gln Ala Leu Gln Lys Gly Ser Phe Lys Thr Ala Asp Ser Leu Pro Gln
            85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
    130                 135                 140

Thr Leu Val Ile Arg Ser Tyr Cys Pro Asn Lys Pro Gly Phe Trp Ala
```

```
                    145                 150                 155                 160
Asp Lys Pro Ile Glu Arg Gln Ala
                165
```

<210> SEQ ID NO 3
<211> LENGTH: 539
<212> TYPE: PRT
<213> ORGANISM: Pseudomonas putida

<400> SEQUENCE: 3

```
Met Ala Asp Thr Asp Thr Gln Lys Ala Asp Val Val Val Gly Ser
 1               5                  10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
                35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
 65                 70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
                115                 120                 125

Asp Trp Pro Ile Gln Tyr Asp Asp Leu Glu Pro Tyr Tyr Gln Arg Ala
        130                 135                 140

Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
                275                 280                 285

Glu Thr Pro Lys Ile Leu Leu Met Ser Ala Asn Arg Asp Phe Pro Asn
                290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
                340                 345                 350
```

```
Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val
    530                 535

<210> SEQ ID NO 4
<211> LENGTH: 27
<212> TYPE: PRT
<213> ORGANISM: Pseudomonas putida

<400> SEQUENCE: 4

Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp
            20                  25

<210> SEQ ID NO 5
<211> LENGTH: 425
<212> TYPE: PRT
<213> ORGANISM: Pseudomonas putida

<400> SEQUENCE: 5

Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp Pro Ala Leu Val Lys
            20                  25                  30

Arg Gly Glu Tyr Leu Ala Thr Ala Met Pro Val Pro Met Leu Gly Lys
        35                  40                  45

Ile Tyr Thr Ser Asn Ile Thr Pro Asp Pro Thr Gly Asp Cys Met
    50                  55                  60

Ala Cys His Thr Val Lys Gly Lys Pro Tyr Ala Gly Gly Leu Gly
65                  70                  75                  80

Gly Ile Gly Lys Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
                100                 105                 110
```

-continued

```
Ser Tyr Ala Lys Ile Lys Asp Asp Val Arg Ala Leu Tyr Ala Tyr
        115             120             125

Phe Met His Gly Val Glu Pro Val Lys Gln Ala Pro Pro Lys Asn Glu
        130             135             140

Ile Pro Ala Leu Leu Ser Met Arg Trp Pro Leu Lys Ile Trp Asn Trp
145             150             155             160

Leu Phe Leu Lys Asp Gly Pro Tyr Gln Pro Lys Pro Ser Gln Ser Ala
                165             170             175

Glu Trp Asn Arg Gly Ala Tyr Leu Val Gln Gly Leu Ala His Cys Ser
            180             185             190

Thr Cys His Thr Pro Arg Gly Ile Ala Met Gln Glu Lys Ser Leu Asp
        195             200             205

Glu Thr Gly Gly Ser Phe Leu Ala Gly Ser Val Leu Ala Gly Trp Asp
        210             215             220

Gly Tyr Asn Ile Thr Ser Asp Pro Asn Ala Gly Ile Gly Ser Trp Thr
225             230             235             240

Gln Gln Gln Leu Val Gln Tyr Leu Arg Thr Gly Ser Val Pro Gly Val
                245             250             255

Ala Gln Ala Ala Gly Pro Met Ala Glu Ala Val Glu His Ser Phe Ser
            260             265             270

Lys Met Thr Glu Ala Asp Ile Gly Ala Ile Ala Thr Tyr Val Arg Thr
        275             280             285

Val Pro Ala Val Ala Asp Ser Asn Ala Lys Gln Pro Arg Ser Ser Trp
        290             295             300

Gly Lys Pro Ala Glu Asp Gly Leu Lys Leu Arg Gly Val Ala Leu Ala
305             310             315             320

Ser Ser Gly Ile Asp Pro Ala Arg Leu Tyr Leu Gly Asn Cys Ala Thr
                325             330             335

Cys His Gln Met Gln Gly Lys Gly Thr Pro Asp Gly Tyr Tyr Pro Ser
            340             345             350

Leu Phe His Asn Ser Thr Val Gly Ala Ser Asn Pro Ser Asn Leu Val
        355             360             365

Gln Val Ile Leu Asn Gly Val Gln Arg Lys Ile Gly Ser Glu Asp Ile
        370             375             380

Gly Met Pro Ala Phe Arg Tyr Asp Leu Asn Asp Ala Gln Ile Ala Ala
385             390             395             400

Leu Thr Asn Tyr Val Thr Ala Gln Phe Gly Asn Pro Ala Ala Lys Val
                405             410             415

Thr Glu Gln Asp Val Ala Lys Leu Arg
            420             425
```